United States Patent [19]

Meyers et al.

[11] Patent Number: 4,601,904
[45] Date of Patent: Jul. 22, 1986

[54] ANTIBIOTICS XYLOCANDIN A AND XYLOCANDIN B

[75] Inventors: Edward Meyers, East Brunswick; Wen-Chih Liu, Princeton Junction; Richard B. Sykes, Belle Mead, all of N.J.

[73] Assignee: E. R. Squibb & Sons, Inc., Princeton, N.J.

[21] Appl. No.: 624,557

[22] Filed: Jun. 25, 1984

Related U.S. Application Data

[63] Continuation-in-part of Ser. No. 474,103, Mar. 10, 1983, abandoned.

[51] Int. Cl.$^4$ .................. A61K 35/00; C12P 1/04; C12N 1/20
[52] U.S. Cl. .................. 424/118; 435/170; 435/253
[58] Field of Search .............. 435/253, 170; 424/118

[56] References Cited

U.S. PATENT DOCUMENTS 4,283,389 8/1981 Ezaki et al. .................. 435/170

OTHER PUBLICATIONS

A.T.C.C. Catalogue of Strains I, p. 172, 15th Ed., 1982.

Primary Examiner—Alvin E. Tanenholtz
Attorney, Agent, or Firm—Lawrence S. Levinson; Donald J. Barrack

[57] ABSTRACT

Cultivation of a strain of the microorganism *Pseudomonas cepacia* which has been deposited in the American Type Culture Collection as A.T.C.C. No. 39277, yields novel antibiotic substances xylocandin A and xylocandin B having activity against yeasts and fungi.

4 Claims, 6 Drawing Figures

FIGURE 1. INFRARED SPECTRUM OF XYLOCANDIN A IN POTASSIUM BROMIDE

400 MHz $^1$H SPECTRUM OF XYLOCANDIN A IN DEUTERATED DIMETHYLSULFOXIDE-DEUTERATED WATER

400 MHz H NMR SPECTRUM OF XYLOCANDIN B IN DEUTERATED DIMETHYLSULFOXIDE-DEUTERATED WATER

ANTIBIOTICS XYLOCANDIN A AND XYLOCANDIN B

This application is a continuation-in-part of copending application Ser. No. 474,103, filed Mar. 10, 1983, and now abandoned.

SUMMARY OF THE INVENTION

Cultivation of a strain of the microorganism *Pseudomonas cepacia*, which has been deposited in the American Type Culture Collection as A.T.C.C. No. 39277, yields novel antibiotic substances xylocandin A and xylocandin B having activity against yeasts and fungi.

DETAILED DESCRIPTION OF THE INVENTION

The Microorganism

Figure 1:
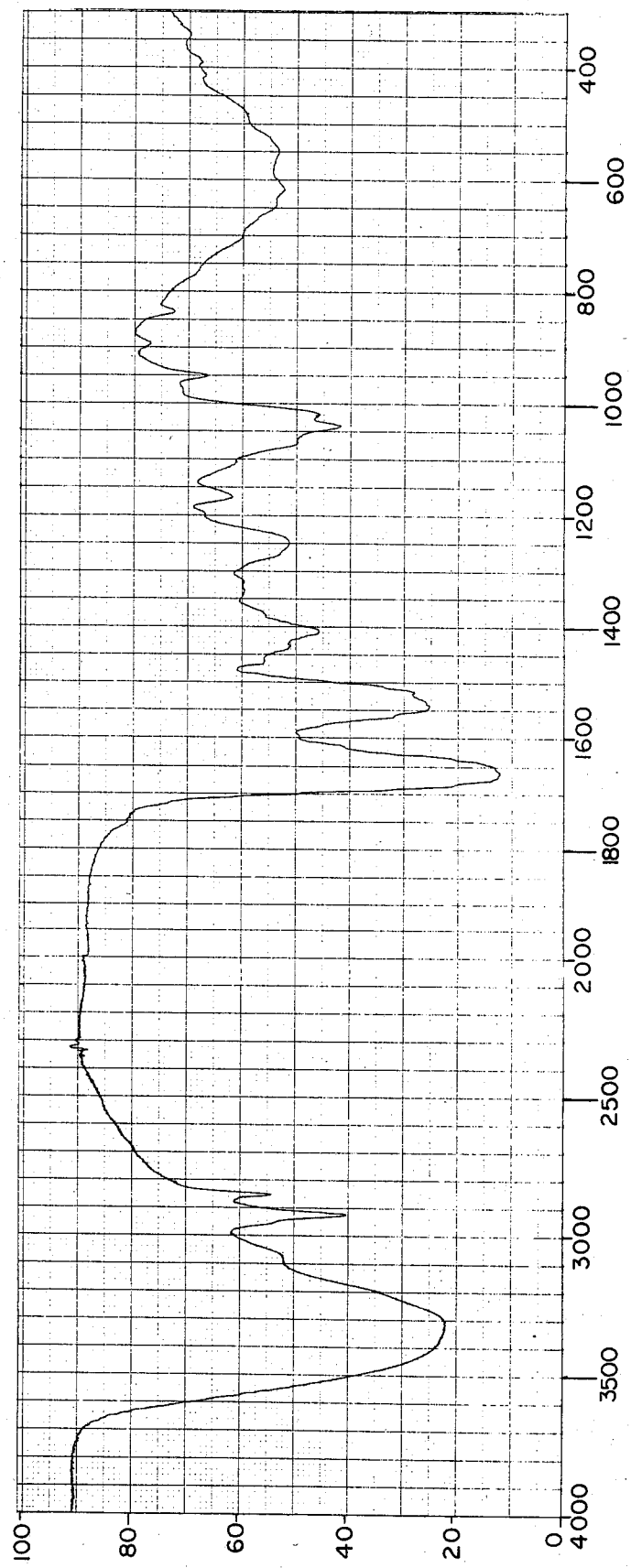
FIG. 1 shows the infrared spectrum of xylocandin A in potassium bromide.

The microorganism used for the production of xylocandin A and xylocandin B is a strain of *Pseudomonas cepacia*. A subculture of the organism can be obtained from the permanent collection of the American Type Culture Collection, Rockville, Md. Its accession number in the repository is A.T.C.C. No. 39277. In addition to the specific microorganism described and characterized herein, it should be understood that mutants of the microorganism (e.g., mutants produced through the use of X-rays, ultraviolet radiation or nitrogen mustards) can also be cultivated to produce xylocandins A and B.

Isolation of *Pseudomonas cepacia* from a soil sample in which it is present can be accomplished by shaking the soil in sterile distilled water and plating appropriate dilutions of the soil suspension on a nutrient agar containing:

|  |  |  |
|---|---|---|
| Compost Extract* | 400 | ml |
| Yeast Extract | 5 | gm |
| Glucose | 10 | gm |
| Agar | 17.5 | gm |
| Tap Water | 600 | ml |

*Compost Extract is made by bringing to a boil a suspension of leaf litter in tap water (2:1, v/v) and then allowing to simmer for about 30 minutes. After cooling, the extract is filtered first through cheesecloth and finally through Whatman 4 filter paper. The resulting liquid is sterilized by autoclaving at 121° C. for 20 minutes.

The medium is adjusted to pH 6.6 and sterilized in an autoclave at 121° C. for 30 minutes. After 2 to 3 days incubation at 25° C., the colonies of *Pseudomonas cepacia* A.T.C.C. No. 39277 are isolated from the plated soil. The isolated colonies are picked off and maintained on an agar medium composed of:

|  |  |  |
|---|---|---|
| Yeast Extract | 1 | g |
| Beef Extract | 1 | g |
| NZ Amine A | 2 | g |
| Glucose | 10 | g |
| Agar | 15 | g |
| Distilled water to | 1000 | ml |

The medium is adjusted to pH 7.3 and sterilized in an autoclave at 121° C. for 30 minutes.

The characteristics of *Pseudomonas cepacia* A.T.C.C. No. 39277 are:

Morphology: The microorganism is a gram negative, polar flagellate, rod. While this strain is pigmentless, the reference culture of *Pseudomonas cepacia* produces a characteristic, yellow, non-fluorescent, water soluble pigment; however, pigmentless variants may arise in platings of the latter. Poly-β-hydroxybutyrate accumulates intracellularly as demonstrated by Burdon's Sudan black stain.

Biochemical characteristics: The microorganism is oxidative in its metabolism, cytochrome oxidase and catalase positive, arginine dihydrolase negative and lysine decarboxylase positive. It is gelatinase positive and nitrate reductase negative. It grows at 41° C.

The following compounds can be utilized as the sole carbon source to grow *Pseudomonas cepacia* A.T.C.C. No. 39277: glucose, xylose, arabinose, fructose, sucrose, ribose, mannitol, sorbitol, salicin, acetate, citrate, cellobiose, L-threonine, putrescine and tryptamine. Those compounds that cannot be utilized as the sole carbon source to grow *Pseudomonas cepacia* A.T.C.C. No. 39277 are: rhamnose, maltose, lactose, erythritol, D-fucose and D-tartrate. Growth on acetamide is weak.

The data presented above conform with the description of *Pseudomonas cepacia* as determined by standard methods for identification of pseudomonads described in Stanier, R. Y. et al. (1966) J. Gen. Microbiol. 43:159, and Ballard, R. W. et al. (1970) J. Gen. Microbiol. 60:199.

Production of the Antibiotic

*Pseudomonas cepacia* A.T.C.C. No. 39277 produces antibiotics xylocandin A and xylocandin B which possess activity against yeasts and fungi. To form antibiotics xylocandin A and xylocandin B according to the preferred method, *Pseudomonas cepacia* A.T.C.C. No. 39277 is grown at, or near, room temperature (25° C.) under submerged aerobic conditions in an aqueous nutrient medium containing an assimilable carbohydrate and nitrogen source. The fermentation is carried out until substantial activity is imparted to the medium, usually about 18 to 48 hours, preferably about 23 to 30 hours.

After the fermentation is complete, the growth is centrifuged to remove the producing microorganism. The supernate, adjusted to pH about 3 with an acid such as hydrochloric acid, is extracted with a mixture of methanol:n-butanol (1:9) and the extract is then concentrated in vacuo. The concentrate is held at 5° C. for several days and the resulting precipitate separated and washed with acetone. The solid is washed with water and then dissolved to the extent possible in dimethylformamide. After removal of insoluble material, the dimethylformamide is removed in vacuo to give a crude mixture of xylocandin A and xylocandin B.

The crude mixture is chromatographed on a column of MCI gel CHP20P*, eluting with dimethylsulfoxide-acetic acid-water mixtures. Xylocandin A elutes first followed by xylocandin B.

*MCI gel CHP20P (Mitsubishi Chemical Industries, Ltd., Japan) is a styrene and divinylbenzene copolymer in a bead form having a macroreticular structure.

Fractions containing the individual components are combined and concentrated in vacuo. The residues are then further purified by gel filtration chromatography on Fractogel TSK HW40** in dimethylsulfoxide to give the pure antibiotics.

**Fractogel TSK HW40 is a semi-rigid hydrophilic vinyl polymer gel available from EM Science, Gibbstown, N.J.

Alternatively, the crude mixture is dissolved in dimethylformamide-acetic acid, 97:3, and placed on a column of Bio-Rad AGMP-50 resin*** (pyridinium form). The column is eluted first with a gradient of 1M aqueous acetic acid to dimethylformamide-water (4:1) which elutes xylocandin B and then with a gradient of 0.1M acetic acid in dimethylformamide-water (3:2) to 2.1M acetic acid and 2.0M pyridine in dimethylformamide-water (3:2) which elutes xylocandin A. Xylocandin A is further purified by gel filtration chromatography and chromatography on MCI gel CHP20P as described above. Xylocandin B (mixed with a third, unidentified component) is further purified by chromatography on MCI gel CHP20P and by gel filtration chromatography as described above.

***Bio-Rad AG MP-50 resin is a strongly acidic cation exchange resin composed of sulfonic acid functional groups attached to a macroporous styrene-divinylbenzene copolymer lattice available from Bio-Rad Laboratories, Richmond, Calif.

Xylocandin A is a basic antibiotic substance that forms acid-addition salts with various organic and inorganic acids. These acid addition salts form an integral part of this invention. Illustrative are the hydrohalides, especially the hydrochloride and hydrobromide, sulfate, nitrate, phosphate, borate, acetate, tartrate, maleate, citrate, succinate, benzoate, ascorbate, salicylate, methanesulfonate, benzenesulfonate, toluenesulfonate and the like.

Acid hydrolysis of xylocandin A yields 2,4-diaminobutyric acid, glycine, serine, aspartic acid, xylose, and unidentified products. Xylocandin A also contains a para-substituted phenolic residue. The nominal molecular weight is 1215.

Xylocandin B is a weakly acidic antibiotic substance. Acid hydrolysis of xylocandin B yields glycine, serine, aspartic acid, xylose and unidentified products. Like xylocandin A, xylocandin B also contains a para-substituted phenol. The nominal molecular weight is 1251.

The following examples further illustrate the preparation of xylocandins A and B.

EXAMPLE 1

Yeast extract, beef extract, NZ amine, glucose agar slants were seeded with *Pseudomonas cepacia* A.T.C.C. No. 39277, incubated overnight at 25° C. and used to inoculate 100 ml portions of an aqueous medium contained in 500 ml Erlenmeyer flasks. The composition of the germination medium is:

| Medium | |
|---|---|
| Yeast extract | 4 g |
| Malt extract | 10 g |
| Dextrose | 4 g |
| Distilled water to | 1,000 ml |

The medium, adjusted to pH 7.3, was sterilized at 121° C. and at 15 lbs steam pressure prior to use. The inoculated germination flasks were incubated at 25° C. for approximately 24 hours on a rotary shaker, operating at 300 r.p.m. with a 2-inch stroke.

A 1% (v/v) transfer was made from the germination flasks to 100 ml portions of fresh yeast extract, malt extract, dextrose medium as described above. The flasks were incubated at 25° C. for approximately 25 to 30 hours, with the same operating conditions as described for the germinator flasks.

EXAMPLE 2

*Pseudomonas cepacia* A.T.C.C. 39277 was maintained on the following sterilized agar medium:

| Yeast Extract | 1.0 g |
|---|---|
| Beef Extract | 1.0 g |
| NZ Amine A | 2.0 g |
| Glucose | 10.0 g |
| Agar | 15.0 g |
| Distilled water to | 1000 ml |

The medium, adjusted to pH 7.3, was sterilized at 121° C. for 30 minutes. A loopful of surface growth was used to inoculate each of four 500 ml Erlenmeyer flasks, each containing 100 ml of the following fermentation medium:

| Yeast Extract | 4.0 g |
|---|---|
| Malt Extract | 10.0 g |
| Dextrose | 4.0 g |
| Distilled water to | 1000 ml |

The medium, adjusted to pH 7.3, was sterilized at 121° C. for 15 minutes. After inoculation, the flasks were incubated at 25° C. on a rotary shaker (300 rpm; 2 inch stroke) for approximately 24 hours, when 1% (vol/vol) transers were made from the grown culture flasks to forty 500 ml Erlenmeyer flasks, each containing 100 ml of fresh fermentation medium. After inoculation, the flasks were once again incubated at 25° C. on a rotary shaker (300 rpm; 2 inch stroke) for approximately 24 hours. A 1% transfer (vol/vol) was made to a 380 liter stainless steel fermentation tank containing 250 liters of fresh, sterilized fermentation medium. After inoculation, the fermentation was continued under the following conditions: temperature 25° C., pressure 10 psig, aeration 10 CFM, agitation 130 rpm. Ucon was added as needed as an antifoam agent. After approximately 23 hours, the fermentation was completed. The contents of the tank were centrifuged yielding approximately 240 liters of supernatant broth.

The broth was extracted with two 125 liter portions of butanol-methanol (9:1) and the extract was concentrated, keeping the pH near 3. The concentrate (ca. 15 liters) was stored at 5° C. for five days, and the deposited precipitate was separated by decantation and centrifugation. The precipitate was washed with acetone and dried in vacuo to afford 52.2 g of tan solid. A 26.4 g portion of this solid was ground finely and stirred with 300 ml of water for one-half hour. The solid was separated by centrifugation and stirred for one-half hour with a second 300 ml portion of water. The remaining solid was separated by centrifugation and, while still moist, was slurried with 300 ml of dimethylformamide while cooling briefly in an ice bath to maintain ambient temperature. The mixture was stirred for one-half hour. The insoluble residue was separated by centrifugation and stirred for one-half hour with a second 300 ml portion of dimethylformamide. The two dimethylformamide solutions were combined and concentrated to afford 2.03 g of crude xylocandins.

A 1.003 g portion of the solid was dissolved in 13 ml of dimethylsulfoxide after which 1 ml of acetic acid and 6 ml of water were added. The mixture was sonicated for 15 minutes, centrifuged and the supernate applied to a 2.5×21 cm (100 ml) column of MCI gel CHP20P packed in dimethylsulfoxide-acetic acid-water, 13:1:6 (system I). The insoluble residue was dissolved to the extent possible in an additional 20 ml of system I as above and the supernate applied to the column. The column was eluted at 1 ml/minute with 500 ml of system I followed by a linear gradient prepared from 2 liters of system I and 2 liters of dimethylsulfoxide-acetic acid, 19:1 (system II), collecting 20 ml fractions. For assay, 200 μl aliquots were concentrated in vacuo, and the residue redissolved in 20 μl of dimethylformamide. One μL samples were spotted on a Merck silica gel 60F TLC plate and dried in a stream of air at room temperature. The plate was eluted at 37° C. with butanol-acetic acid-water, 4:1:5 (upper phase), dried in vacuo and the xylocandin components visualized by the Rydon-Smith method. Xylocandin A has $R_f$ 0.20 and xylocandin B has $R_f$ 0.23. Fractions 12~15 contained xylocandin A, 16~22 a mixture of xylocandin A and an impurity, and 49~56 xylocandin B.

Fractions 12~15 were combined and concentrated at 0.03 mm of Hg and 45° C. to a small volume. The product was precipitated by the addition of ethyl acetate, washed with two portions of ethyl acetate and dried in vacuo to give 172.2 mg of xylocandin A. Fractions 16~22 were concentrated, dissolved in system I and rechromatographed on the same MCI gel CHP20P column, eluting at 1 ml/minute with system I and collecting 20 ml fractions. Fractions 12~15 were worked up as above to give an additional 46.5 mg of xylocandin A. The combined xylocandin A weighed, 224.7 mg.

Fractions 49~56 were combined, concentrated to a small volume at 40° C. and 0.03 mm of Hg and mixed with ethyl acetate. The resulting precipitate was separated by centrifugation, washed with ethyl acetate, and dried in vacuo to give 56.7 mg of crude xylocandin B as a tan solid.

The solid was dissolved in 1.1 ml of dimethylsulfoxide and applied to a 2.5×22 cm (100 ml) column of Fractogel TSK HW40 packed in dimethylsulfoxide. The column was eluted at 1 ml/minute and 5 ml fractions were collected. Fractions 14~16 (which contained only xylocandin B by TLC) were combined, concentrated, and treated with ethyl acetate to give 35.6 mg of solid. The $^1$H NMR spectrum indicated that the solid contained one equivalent of dimethylsulfoxide.

Elemental analysis of xylocandin B was done on a sample dried in vacuo at 50° C. for 1 hour that contained approximately one equivalent of dimethylsulfoxide. Found: C, 50.43; H, 7.05; N, 12.17.

Figure 4:
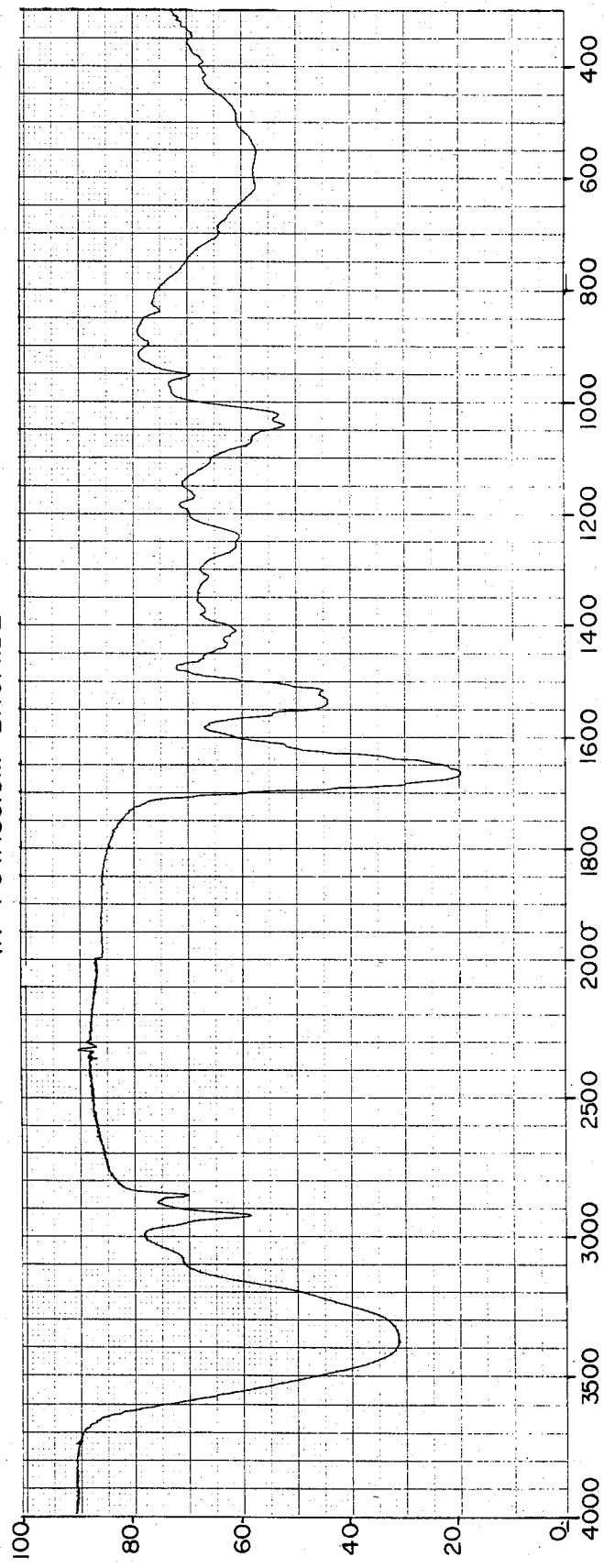
FIG. 4 shows the infrared spectrum of xylocandin B in potassium bromide.

The infrared spectrum of xylocandin B in potassium bromide is shown in FIG. 4.

Figure 5:
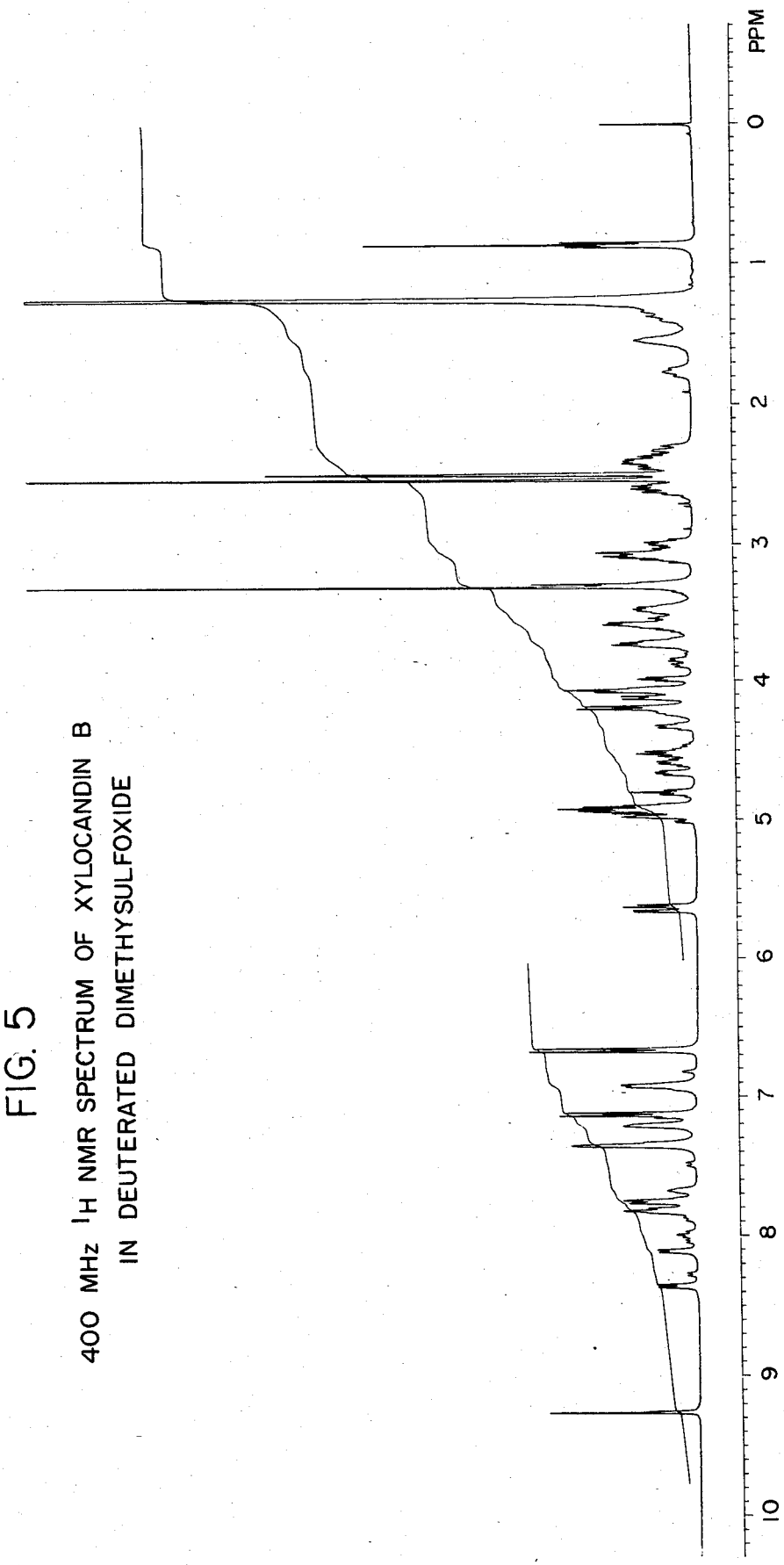
FIG. 5 shows the 400 MHz $^1$H NMR spectrum of xylocandin B in deuterated dimethylsulfoxide.

The 400 MHz $^1$H NMR spectrum of xylocandin B in deuterated dimethylsulfoxide is shown in FIG. 5.

Figure 6:
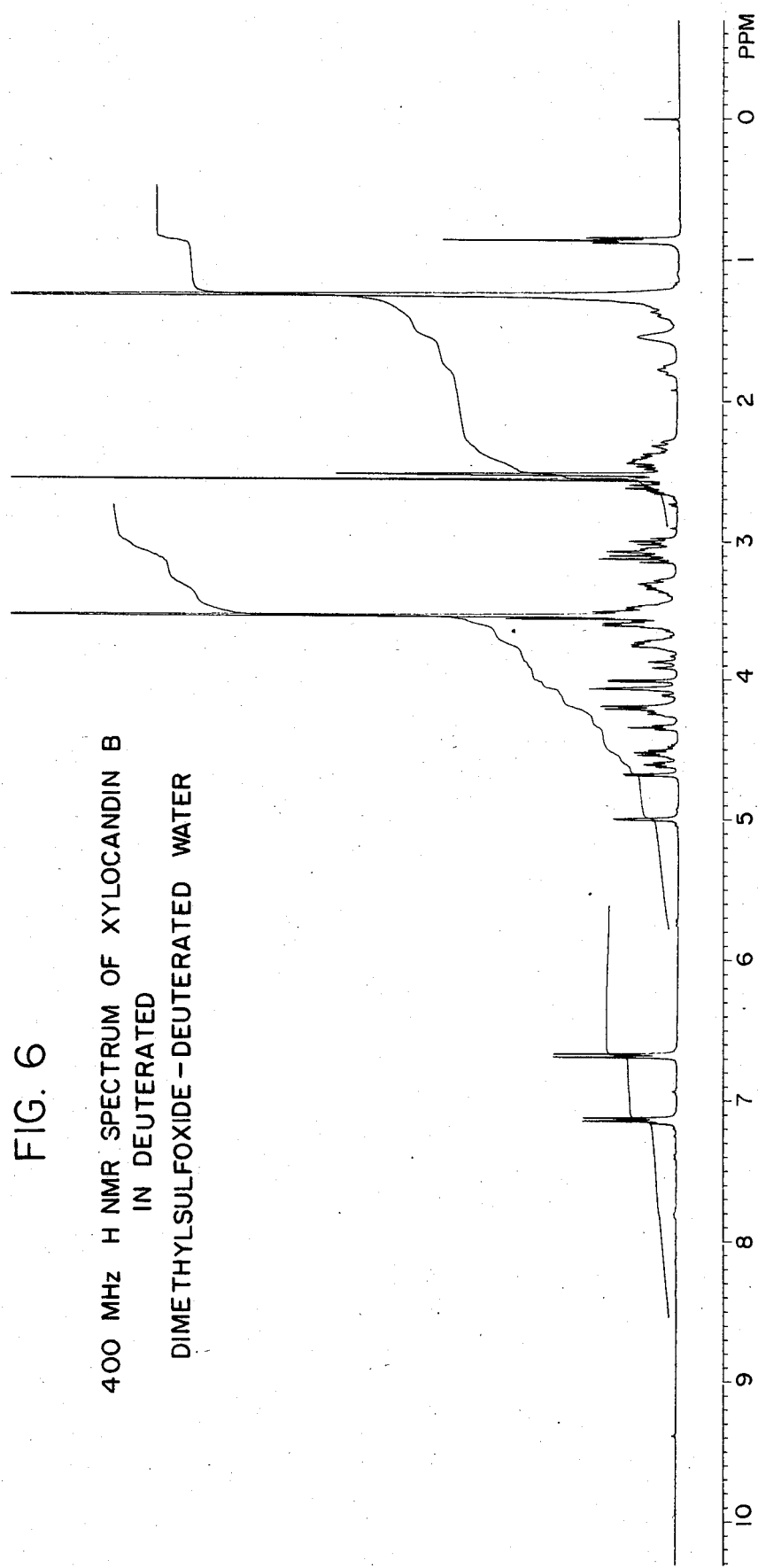
FIG. 6 shows the 400 MHz $^1$H NMR spectrum of xylocandin B in deuterated dimethylsulfoxide-deuterated water (20:1).

The 400 MHz $^1$H NMR spectrum of xylocandin B in deuterated dimethylsulfoxide-deuterated water (20:1) is shown in FIG. 6.

The UV spectrum of xylocandin B in dimethylsulfoxide shows: λmax ($E^{1\%}$) 278 (14.6), 284 nm (sh, 12.6).

Both xylocandin A and xylocandin B are easily soluble in dimethylformamide and dimethylsulfoxide. They have very little solubility in water, methanol, ethanol, acetone and ethyl acetate.

Alternatively, 1.95 g of a crude mixture of xylocandin A and B obtained via the methodology described above was dissolved in 9 ml of dimethylformamide-acetic acid (97:3) and stirred briefly with 2 ml of water-wet Bio-Rad AG MP-50 ion exchange resin in the pyridinium form. The slurry was loaded onto a column (2.5×30 cm) of Bio-Rad AGMP-50 resin, (pyridinium form) packed in 1M aqueous acetic acid and the column was eluted with 1600 ml of linear gradient beginning with 1M aqueous acetic acid and ending with dimethylformamide-water (4:1), collecting 20 ml fractions. TLC assay was carried out as described above. Fractions 31-69 contained xylocandin B. These fractions were combined and concentrated to a residue which could then be chromatographed on MCI gel CHP20P and Fractogel TSK HW40 as described above to afford pure xylocandin B. The Bio-Rad AG MP-50 column was then eluted with 1600 ml of a linear gradient beginning with 0.1M acetic acid in dimethylformamide-water, (3:2) and ending with 2.1M acetic acid and 2.0M pyridine in dimethylformamide-water, (3:2), collecting 20 ml fractions. This was followed by elution with 1 liter of the final buffer. Fractions 17-30 contained xylocandin A contaminated with a trace of an unknown, lower $R_f$ impurity. Fractions 31-59 contained xylocandin A with traces of higher $R_f$ impurities. Fractions 60-70 and the 1 liter fraction contained xylocandin A with greater amounts of higher $R_f$ impurities. Fractions 31-59 were combined, concentrated to near dryness and redissolved in a small volume of dimethylsulfoxide. The product was precipitated by the addition of tetrahydrofuran, washed twice with tetrahydrofuran and dried in vacuo to afford 230 mg of a light brown solid. A total of 278 mg of solid prepared in this fashion was dissolved in 1 ml of dimethylsulfoxide and eluted through a column (2.5×28 cm) of Fractogel TSK HW40 at a rate of 0.25 ml/minute, collecting 2 ml fractions. Fractions 40-70 were combined and concentrated to a semisolid residue. This was dissolved in 4 ml dimethylsulfoxide-acetic acid-water, 13:1:6 (system I), and applied to a column (2.5×26 cm) of CHP20P resin packed in system I. The column was eluted at a rate of 0.75 ml/minute with system I, collecting 6 ml fractions. Fractions 32-50 (which contained only xylocandin A by TLC) were combined, concentrated to a small volume and precipitated by ethyl acetate. The precipitate was washed twice with ethyl acetate and dried in vacuo to give 122 mg of a white solid. The $^1$H NMR spectrum indicated that the solid contained 0.82 equivalents of acetic acid and 1.5 equivalents of dimethylsulfoxide.

Elemental analysis of xylocandin A was done on a sample dried in vacuo at 50° C. for 1 hour that contained 0.82 equivalents of acetic acid and 1.5 equivalents of dimethylsulfoxide.

Found: C, 47.39; H, 7.02; N, 10.57.

The infrared spectrum of xylocandin A in potassium bromide is shown in FIG. 1.

Figure 2:
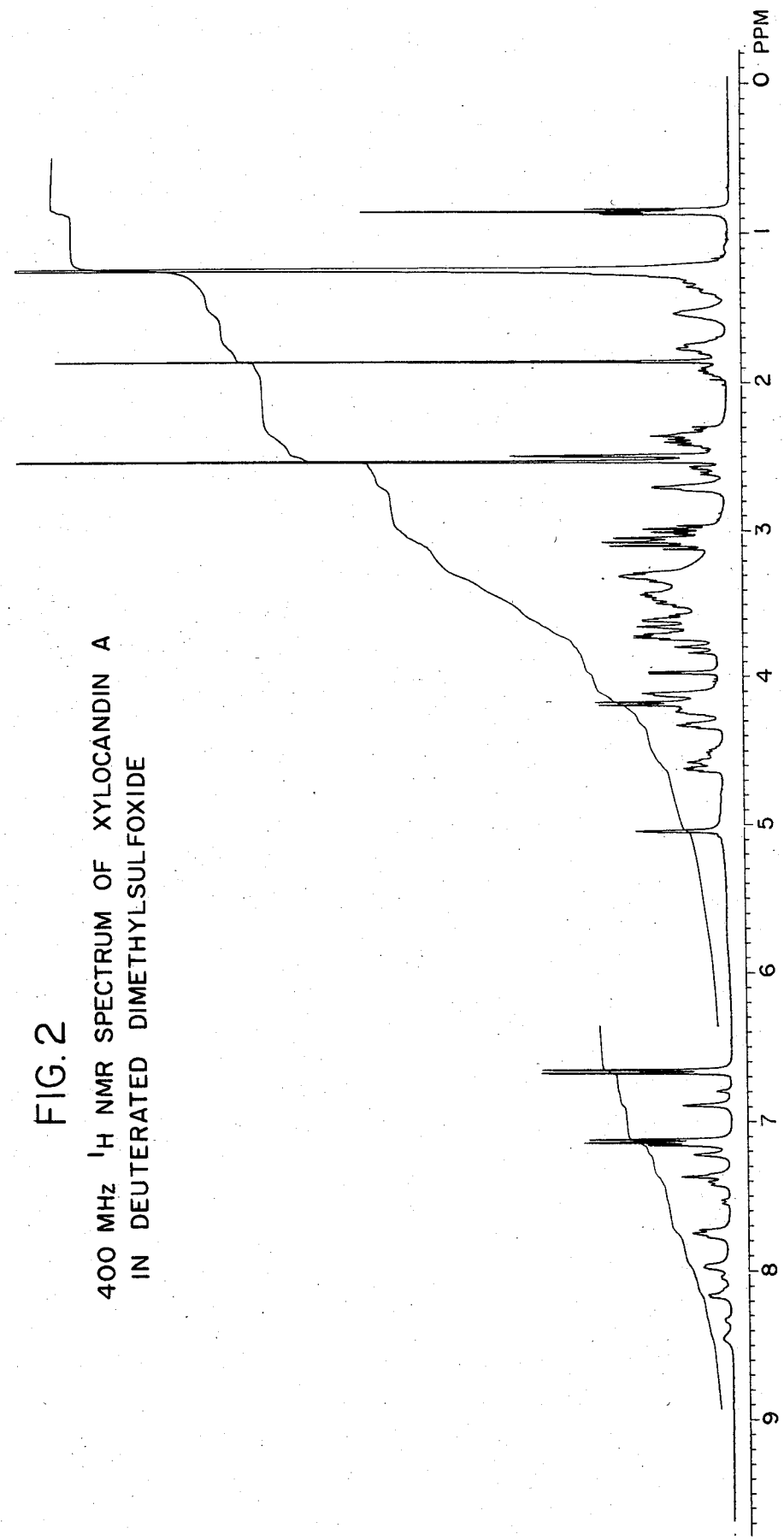
FIG. 2 shows the 400 MHz $^1$H NMR spectrum of xylocandin A in deuterated dimethylsulfoxide.

The 400 MHz $^1$H NMR spectrum of xylocandin A in deuterated dimethylsulfoxide is shown in FIG. 2.

Figure 3:
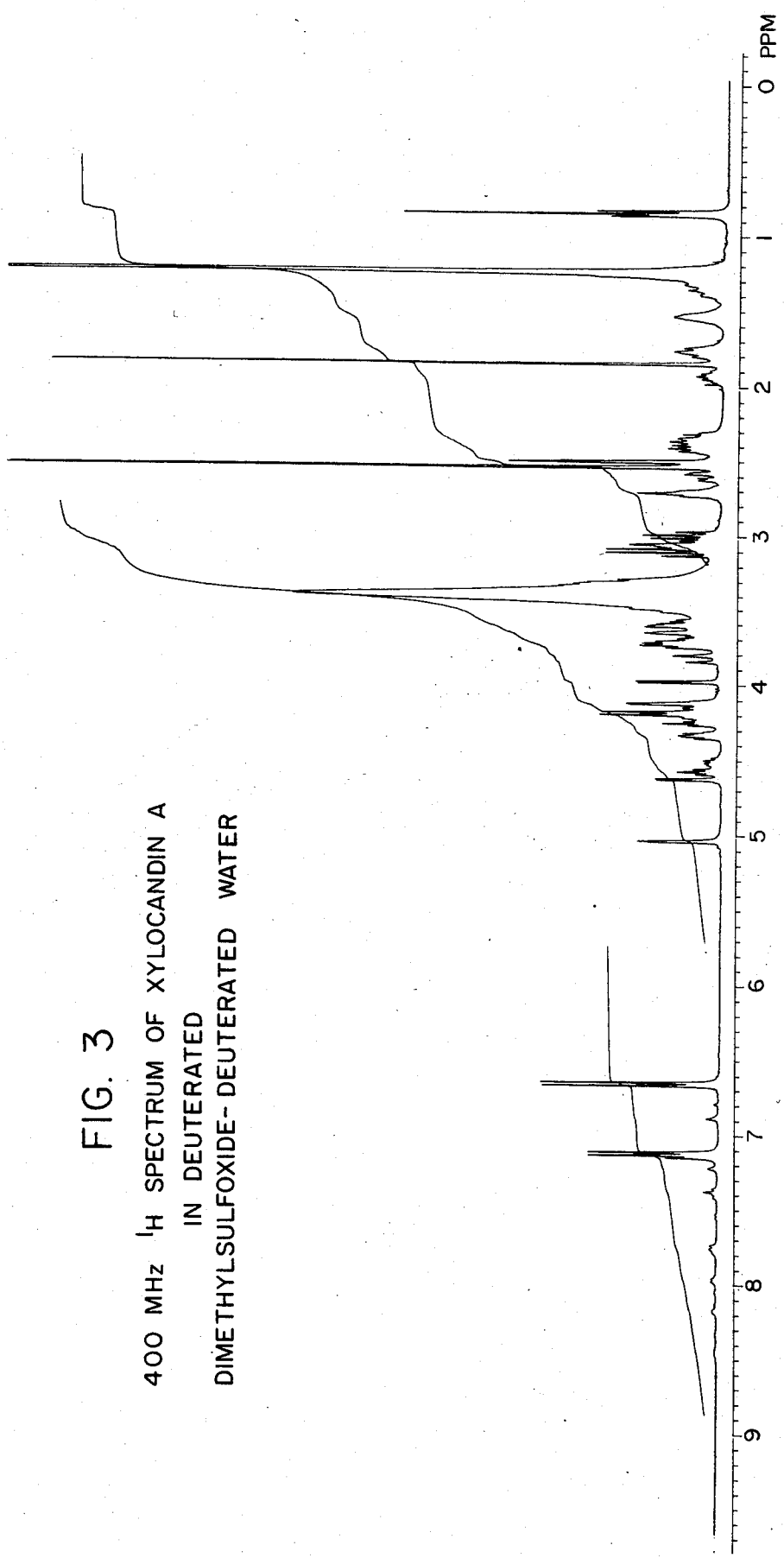
FIG. 3 shows the 400 MHz $^1$H NMR spectrum of xylocandin A in deuterated dimethylsulfoxide-deuterated water (10:1).

The 400 MHz $^1$H NMR spectrum of xylocandin A in deuterated dimethylsulfoxide-deuterated water (10:1) is shown in FIG. 3.

The UV spectrum of xylocandin A in dimethylsulfoxide shows: λmax ($E^{1\%}$) 278 (12.1), 284 nm (sh, 10.3).

Biological Activity

Two fold agar dilution assay of xylocandin A and xylocandin B with several strains of Candida showed the following results:

| Organism | SC No.** | MIC (μg/ml) Xylocandin A | MIC (μg/ml) Xylocandin B |
| --- | --- | --- | --- |
| Candida albicans | 5314 | 0.2 | 3.1 |
| Candida albicans | 9177 | 0.4 | 3.1 |
| Candida albicans | 11,422 | 0.4 | 6.3 |
| Candida albicans | 10,580 | 0.4 | 3.1 |
| Candida albicans | 10,102 | 0.4 | 3.1 |
| Candida albicans | 9721 | 0.2 | 3.1 |
| Candida albicans (Bacilysin$^R$)* | 12,734 | 0.2 | 3.1 |
| Candida albicans (Aculeacin$^R$) | DKY53 | 0.4 | 3.1 |
| Candida albicans | 10,584 | 0.4 | 3.1 |
| Candida albicans | 10,585 | 0.1 | 3.1 |
| Candida tropicalis | 8159 | 0.2 | 6.3 |
| Candida tropicalis (Amphotericin $B^R$) | 2963 | 0.2 | 6.3 |
| Candida tropicalis (Amphotericin $B^R$) | 9861 | 0.2 | 25 |
| Candida tropicalis | 10,597 | 0.1 | 3.1 |
| Candida krusei (Amphotericin $B^R$) | 2967 | 0.4 | 25 |
| Candida krusei (Nystatin$^R$) | 2969 | 0.4 | 6.3 |
| Candida krusei | 2968 | 0.4 | 6.3 |
| Candida parakrusei | 2621 | 1.6 | 25 |
| Candida parakrusei | 2966 | 0.2 | 6.3 |
| Candida pseudotropicalis | 11,241 | 0.2 | 6.3 |
| Candida guilliermondii | 2210 | 0.4 | 6.3 |
| Candida guilliermondii (Amphotericin $B^R$) | 2996 | 0.8 | 6.3 |
| Candida stellatoidea | 2211 | 0.4 | 6.3 |
| Candida glabrata | 9342 | 0.4 | 6.3 |
| Candida glabrata | 11,267 | 0.4 | 6.3 |

*($^R$) indicates that the organism is resistant to the antibiotic named.
**SC No. is the number in the microorganism collection of E. R. Squibb & Sons, Inc., Princeton, New Jersey.

Xylocandin A is active against dermatophytes (agar dilution assay).

| Organism | SC No. | MIC (μg/ml) |
| --- | --- | --- |
| Trichophyton mentagrophytes | 2637 | 0.1 |
| Epidermophyton floccosum | 9185 | <0.05 |
| Trichophyton rubrum | 9199 | 0.2 |
| Microsporum canis | 9237 | <0.05 |

What is claimed is:

1. Substantially pure xylocandin A, or an acid addition salt thereof, having the approximate elemental analysis C, 47.39; H, 7.02; N, 10.57; and having the infrared spectrum in potassium bromide shown in FIG. 1, the 400 MHz $^1$H NMR spectrum in deuterated dimethylsulfoxide shown in FIG. 2 and the 400 MHz $^1$H NMR spectrum in deuterated dimethylsulfoxide-deuterated water (10:1) shown in FIG. 3.

2. Substantially pure xylocandin B, having the approximate elemental analysis C, 50.43; H, 7.05; N, 12.17; and having the infrared spectrum in potassium bromide shown in FIG. 4, the 400 MHz $^1$H NMR spectrum in deuterated dimethylsulfoxide shown in FIG. 5 and the 400 MHz $^1$H NMR spectrum in deuterated dimethylsulfoxide-deuterated water (20:1) shown in FIG. 6.

3. A process for preparing xylocandin A and xylocandin B which comprises cultivating *Pseudomonas cepacia* A.T.C.C. No. 39277 in an aqueous nutrient medium containing an assimilable carbohydrate and nitrogen source under submerged aerobic conditions until substantial antibiotic activity is imparted to the medium and isolating xylocandin A, xylocandin B or both xylocandin A and xylocandin B.

4. A process in accordance with claim 3 wherein the microorganism is cultivated at about 25° C.

* * * * *